United States Patent [19]

Simon et al.

[11] Patent Number: 4,592,488

[45] Date of Patent: * Jun. 3, 1986

[54] METHOD FOR THE PREPARATION OF CHEMOTHERAPEUTIC COMPOSITIONS FOR THE TREATMENT OF PERIODONTAL DISEASE, COMPOSITIONS THEREFOR AND USE THEREOF

[76] Inventors: Gilbert I. Simon, 111 Midland Ave., Bronxville, N.Y. 10708; Roy T. Witkin, 23 Broadview Rd., Westport, Conn. 06880

[*] Notice: The portion of the term of this patent subsequent to Jun. 4, 2002 has been disclaimed.

[21] Appl. No.: 737,469

[22] Filed: May 24, 1985

[51] Int. Cl.$^4$ ............... A61K 7/20; A61K 33/18; A61K 31/79

[52] U.S. Cl. ................... 222/94; 424/51; 424/53

[58] Field of Search ............ 424/51, 53; 222/94

[56] References Cited

U.S. PATENT DOCUMENTS

| 1,535,529 | 4/1925 | Hopkins | 424/53 |
|---|---|---|---|
| 1,566,218 | 12/1925 | Leland | 424/49 |
| 2,789,731 | 4/1957 | Marrafino | 222/129 |
| 3,874,558 | 4/1975 | Rockefeller | 222/92 |
| 4,060,179 | 11/1977 | McGhie | 222/92 |
| 4,098,435 | 7/1978 | Weyn | 222/94 |
| 4,211,341 | 7/1980 | Weyn | 222/94 |
| 4,330,531 | 5/1982 | Alliger | 424/53 |
| 4,335,110 | 6/1982 | Collins | 424/145 |
| 4,487,757 | 12/1984 | Kiozpeoplou | 424/7.1 |
| 4,521,403 | 6/1985 | Simon et al. | 424/51 |
| 4,528,180 | 7/1985 | Schaeffer | 424/52 |

OTHER PUBLICATIONS

"PVP–Iodine 30/06", BASF Publication, Register 4, 9/80.

Primary Examiner—Shep K. Rose
Attorney, Agent, or Firm—Jacobs & Jacobs

[57] ABSTRACT

A method is described for controlling and treating microorganisms implicated in diseases of the teeth and periodontium by applying to the teeth and periodontium an oral lavage comprised of an admixture of selected antimicrobial agents and selected oxygenating agents in predetermined proportions, and compositions therefor and use thereof.

18 Claims, No Drawings

METHOD FOR THE PREPARATION OF CHEMOTHERAPEUTIC COMPOSITIONS FOR THE TREATMENT OF PERIODONTAL DISEASE, COMPOSITIONS THEREFOR AND USE THEREOF

The present invention relates to the treatment of diseases of the periodontium and teeth in the oral cavity of humans for the purpose of destroying or diminishing microbial growth and reducing or retarding accretion of plaque on the teeth by means of a chemotherapeutic composition and method of preparing the same and applying it to inhibit or destroy the major pathogens normally present. The invention comprises a compositon including an antimicrobial agent which is an iodophor or a quaternary ammonium compound and a peroxy compound which is hydrogen peroxide or carbamide or other peroxide, each of which may be in the form of an aqueous or aqueous alcoholic solution prior to combining a pair of them to form an oral lavage, and a method of treating periodontal disease by applying the oral lavage to the oral cavity by rinsing or irrigation. The invention further includes a compartmented or segmented package or container in which the antimicrobial agent and the peroxide components can be kept out of physical contact with one another to avoid premature interaction until the oral lavage components are to be combined ready for use or the components may be pre-mixed and stabilized, i.e. packaged as a combined mixture which is appropriately stabilized and free from impurities which might cause catalytic decompositon of the peroxide.

BACKGROUND OF THE INVENTION

Diseases of the periodontium and teeth caused by microorganisms are prevalent worldwide and these microorganisms are the primary cause of disease of the periodontium and tooth decay and loss in adults.

After teeth are cleaned, they soon become coated with "plaque" which is comprised of organic deposits from saliva, desquamated epithelial cells and masses or oral microorganisms which not only cause cavities in the teeth, but are also believed to be the cause of chronic disease of the periodontal tissues.

The customary techniques heretofore employed for removing plaque and the bacteria contained therein surrounding the teeth is mechanical scaling or root planing of the teeth by a dentist or oral hygienist or flossing and brushing of the teeth by the patient.

The specific identity of the microorganisms which cause periodontal diseases may vary. Pathogens which have been implicated as causing periodontal disease include *Actinomyces viscosus* (ATCC 19246), *Bacteroides intermedius* (ATCC 33563), *Bacteroides gingivalis* (ATCC 33277), *Fusobacterium nucleatum, Staphylococcus aureus* (ATCC 6538), *Candida albicans* (ATCC 10231) and *E. Coli* virus. Although certain materials such as alcohol, iodine and the like have been used in the preparation of oral lavages or antiseptics to control periodontal disease, none of these has been found to be sufficiently effective in controlling the causative microorganisms and hence the disease.

Recent research has shown that periodontal disease can be controlled and treated by the use of certain topically applied antimicrobial agents. Chlorhexidine has, for example, been proved effective in treating periodontal disease. However, the Federal Drug Administration has not permitted this topical agent to be marketed in the United States because of toxicity or cosmetic problems, even though the agent has been shown to be effective in the treatment of periodontal disease. There is thus still a need for an effective oral lavage to treat and control periodontal disease and which is cosmetically acceptable and free of toxicity problems.

Recently, Dr. Paul H. Keyes and Associates proposed a method for controlling periodontal disease by daily brushing of the teeth and gums with a dentifrice comprised of a thick mixture of baking soda moistened with a 3% solution of hydrogen peroxide. Following brushing of the teeth and massaging of the gums with this paste, the mouth is rinsed with salt water. Although this technique has received considerable publicity and has been used by many individuals, its claimed benefits have not been substantiated or reproduced by controlled experimentation. In addition, the high sodium concentration of ingredients used in this technique may be undesirable for use by individuals suffering from hypertension.

Although, in theory, a wide variety of antimicrobial agents and "oxygenating" agents may be and have been considered as components for the antimicrobial compositions embodied in this invention, practical selections are limited by the chemical compatibility of prospective pairs, the physico-chemical properties of the components and their mixtures, including solubility, pH and viscosity, and by safety in use which is dependent on various toxicological characteristics. Some pairs are mutually incompatible, thus yielding mixtures whose effectiveness in ameliorating periodontal disease are in fact effectively less than that of the components.

In our application Ser. No. 565,661 filed Dec. 30, 1983, now U.S. Pat. No. 4,521,403, issued June 4, 1985, we have described an oral lavage and its preparation, which oral lavage comprises povidone iodine complex (PVP-I) and hydrogen peroxide ($H_2O_2$), and its application to the periodontium and teeth wherein the oral lavage has enhanced antimicrobial and anti-plaque activity, particularly when the PVP-I and the $H_2O_2$ are in certain proportional relationships and concentrations. The use of the PVP-I and $H_2O_2$ in combination as an aqueous or aqueous alcoholic solution for the indicated purposes has in particular been found to be very highly effective against the bacteria *Actinomyces viscosus* (ATCC #19246), *Bacteroides intermedius* (ATCC #33563) and *Bacteroides gingivalis* (ATCC #33277). The PVP-I and the $H_2O_2$ are most effective when they are formulated as a freshly prepared aqueous or aqueous alcoholic solution; and when kept physically out of contact with one another in a suitable segmented or compartmented package or container, they have a very satisfactory shelf life up to at least about 6 months. The contents of said application are hereby fully incorporated herein by reference.

PVP-I is well known as a complex or adduct of polyvinylpyrrolidine and iodine and is readily soluble in water. The PVP-I is known as a topical disinfectant which is considered to be due to the release of iodine in aqueous or aqueous alcoholic solution. However, the PVP-I complex by itself is characterized by an insufficient antimicrobial action to ensure destruction or inhibition of the major aerobic and anaerobic pathogens generally present in the oral cavity of humans and recognition of this leads to the requirement for the presence of a peroxy compound or oxidizing agent which releases oxygen to enhance the antimicrobial activity of the PVP-I and to provide protection against the build up of plaque on the teeth.

While there are other ways of destroying the pathogens or inhibiting plaque formation on the teeth, such usually involve cleaning or abrasive and/or anti-infective materials and if not properly formulated are capable of damaging the dentine or enamel of the teeth and have insufficient antimicrobial and anti-plaque action to obtain the benefits of the present invention and hence form no part thereof.

It is also known that $H_2O_2$ is a mild topical anti-infective agent but aqueous solutions of high concentration of $H_2O_2$ would be detrimental if applied to the periodontium and to human tissue and teeth so that it is necessary to use a weak or mild solution of $H_2O_2$, preferably not exceeding 3% and/or to use the $H_2O_2$ in predetermined proportion with relation to the PVP-I.

THE PRESENT INVENTION

The oral lavage mixtures used in the method of the present invention are prepared by formulating the components as solutions, dispersions, or emulsions, with the liquid phases being selected from water, ethanol, glycerol, or other solvents acceptable for contact with oral mucosa and having the desired physico-chemical relationship to the active components. Mixtures of two or more of the above are also suitable in certain cases. In many instances it is convenient to dissolve, disperse or emulsify the active components independently in a suitable solvent taken from the above list and then admix the solvates to form the oral lavage.

Formulations of the individual components can be prepared by techniques per se well known in the art and are then packaged separately or in combination and dispensed from the package either as individual components which become admixed or dispensed together in combination in proportions and amounts described hereinafter. The resulting products are applied as an oral rinse or irrigation as explained in our prior application and exert a similar therapeutic effect.

Flavored or sweetened compositions may be prepared to improve the palatability and patient acceptance of some of the oral lavages by adding commonly recognized flavoring or sweetening ingredients in appropriate amounts to one of the components, usually the antimicrobial agent, before admixing the components or incorporated in the pre-mix or combination compositions. Flavoring ingredients, which are generally recognized as mouthwash additives are used; for example flavorings such as peppermint, spearmint, wintergreen, eucalyptus, menthol, cinnamon and clove, and/or sweeteners such as saccharin, aspartame and sorbitol, and various combinations thereof.

Further advantages of the present oral lavage may be achieved by incorporating a fluoride such as stannous fluoride or sodium fluoride, or sodium monofluorophosphate, etc. to provide an anticavity effect to protect roots and other vulnerable parts of the teeth which may be exposed during periodontal probing, irrigation, surgical treatment, etc.

Since the lavage is preferably intended to be used shortly after the components are admixed or combined, the question of stability of the admixture is only a short-term consideration. Effectiveness of the following pairs for antimicrobial activity has been demonstrated by mixing appropriate concentrations in 1:1 (v/v) proportions and observing for rapid gas evolution, color change, heat evolution, and loss of titer of the active moiety (e.g., quaternary ammonium, active iodine, etc.).

Representative or preferred antimicrobial compositions in accordance with the invention can be illustrated as follows:

| Antimicrobial | $H_2O_2$ | Carbamide Peroxide |
|---|---|---|
| 1. Cetylpyridinium chloride | x | x |
| 2. Biopal (GAF Corp., NY) (nonylphenoxypoly-(ethyleneoxy)ethanol iodine complex) | x | x |
| 3. Polyvinylpyrrolidone-iodine | x | x | x signifies achievement in vitro of enhanced antimicrobial activity by means of oxygen from the peroxide

DESCRIPTION OF THE PRESENT INVENTION

It has now been found in accordance with the present invention that antimicrobial agents other than PVP-I, and PVP-I with oxidizing agents other than $H_2O_2$ are also effective and satisfactory for treatment of the periodontium and teeth. This is obtained by means of a solution containing the antimicrobial agent in combination with $H_2O_2$, carbamide peroxide, benzoyl peroxide, sodium peroxycarbonate or other source of $H_2O_2$ or oxygen to enhance the antimicrobial activity of the antimicrobial agent. In such alternative solutions the PVP-I above referred to is replaced by a quaternary ammonium compound having a $+N_4$ ion and represented by cetylpyridinium chloride which is commercially available as a white crystalline water-soluble powder, or by the iodophor known as Biopal(VRO-20) (GAF Corp., N.Y.) which is a proprietaty water-soluble complex containing 20% titratable iodine. These materials each have some degree of topical disinfecting activity but have not heretofore been used for the purposes of the present invention in conjunction with either $H_2O_2$ or carbamide peroxide or other source of $H_2O_2$ or oxygen to enhance antimicrobial activity of an antimicrobial agent for the treatment of periodontal disease.

Alternative quaternary ammonium compounds to replace cetylpyridinium chloride include benzalkonium chloride, i.e. compounds having an available tetravalent nitrogen atom $+N_4$ or by nonylphenoxypolyethyleneoxyethanol.

The term "enhance" or "enhanced" as used herein means the obtaining of more than an additive antimicrobial effect of the components, since a mere additive action wherein each component only provides its own expected activity does not fall within the ambit of the invention which requires a greater than additive action to attain the objective of this invention.

According to one embodiment of the present invention, cetylpyridinium chloride is used together with either $H_2O_2$ or carbamide peroxide as an oral lavage solution, preferably in predetermined proportions such as but not limited to 1:1 (v/v) which gives peak antimicrobial activity, i.e. proportions wherein the oxygen released from the peroxide maximally enhances the cidal action of the antimicrobial agent.

According to another embodiment of the invention, it has been found that the above stated iodophor Biopal (VRO-20) when used with predetermined proportions of $H_2O_2$ or carbamide peroxide have highly effective and greatly enhanced antimicrobial action against the major pathogens found in the oral cavity and also exert a high degree of anti-plaque activity. These examples are set forth in the table supra.

As in the povidone iodine complex with $H_2O_2$ of our copending application, the peroxide requires special handling and packaging since it is when the two active components are freshly admixed that optimum antimicrobial results are obtained. Thus similar general considerations are involved as in our aforesaid application in that the antimicrobial agent and the oxygen-releasing compound are kept physically out of contact with one another until it is desired to combine or admix them for introduction into the oral cavity for the indicated purposes. As stated above, however, the antimicrobial agent and the source of $H_2O_2$ or oxygen may be premixed as a stabilized combination and packaged as a mixture appropriately stabilized against premature interaction or decomposition.

In further exemplifications of the invention, an oral lavage is prepared by admixing equal volumes of 10% aqueous povidone-iodine and 8.3% glycerol solution of carbamide peroxide. The resulting composition contained 5% povidone-iodine and 4.15% carbamide peroxide.

An oral lavage according to this invention is prepared by admixing equal volumes of a 0.1% aqueous cetylpyridinium chloride solution containing 0.25% peppermint flavor oil (Haarmann & Reimer 01-10310) and 0.35% wintergreen (Haarmann & Reimer 01-10309) and 8.3% aqueous carbamide peroxide solution.

A further oral lavage is prepared by admixing equal volumes of 5% aqueous Biopal containing 0.5% peppermint flavor oil (Haarmann & Reimer 01-10310) and 8.3% glycerol solution of carbamide peroxide.

The oral lavages or compositions of this invention should preferably be used soon after the peroxide-containing agent is admixed with the antimicrobial agent in the defined range or proportions for best antimicrobial results. The oral lavage may be applied to teeth, gums and other teeth supporting structures by rinsing the mouth in the same general manner as with a conventional mouthwash. While the intensity of the periodontal disease may vary with the individual, effective treatment has been observed when the oral lavage is retained in the mouth for about 10 to about 40 seconds. Rinsing the mouth in this manner is preferably effected from about three to about seven times per week. However, the frequency and quantity of the application may be varied for each individual. After use, the oral lavage is expectorated or expelled.

Highly effective results are achieved if the solution is also used by the dentist by irrigation of the periodontium and teeth by a standard irrigating device known in the dental art. Applying the oral lavage between the gums and teeth, preferably below the gum line, by an irrigating device has been found to be a superior effective means of controlling periodontal disease.

Both mechanically and chemotherapeutically, the surprising and unexpected activity of the admixtures of the invention as compared to their individual components may be attributed to the interactions which occur when the components are combined or admixed and the lavage is introduced into the oral cavity; viz:

1. The antimicrobial agent exerts its antimicrobial/antibacterial activity upon certain species of bacteria in the mouth including those specified above which are known to be implicated in periodontal disease.

2. The oxygenating agent primarily exerts an enhancing effect on the antimicrobial activity of the antimicrobial agent but also itself exerts a limited degree of antibacterial activity and in addition releases active or nascent oxygen which appears to have a weakening effect upon the anaerobic bacteria, probably making them more vulnerable to the main antimicrobial agent and furthermore exerts a physically helpful influence upon the infected areas by frothing and debriding and mechanically floating or washing out organic debris and bacteria from the crevices and disease "pockets".

3. To a measurable degree the presence of the antimicrobial agent stimulates release of oxygen from the oxygenating agent, thus enhancing the effects described under 2. Hence the total effect of the combination of active agents in the oral lavage formulations is shown to be surprisingly greater than one would calculate or predict on the basis of the properties of the individual components.

When, as above stated, the antimicrobial agent and the oxygenating or peroxy compound are pre-mixed and packaged as a combination rather than as individual segregated solutions or components, the packaged mixture comprises 10% PVP-I (1:1 v/v) and 3% $H_2O_2$ or relatively equal amounts (v/v) of any of the other herein described compatible pairs of components, and the premixture in the package is suitably stabilized such as by an inert gaseous material exemplified by nitrogen or carbon dioxide, particularly by stabilization of the peroxide and freedom from impurities which might catalyze $H_2O_2$ decomposition. The stabilized combination can be released from its package by opening the package or removing any barrier or plug and the package contents emptied into a receptacle from which it can be taken for introduction into the human oral cavity by rinsing or irrigation techniques.

The concentrations and ratios of the active components of the oral lavages embodied in this invention depend on the respective antimicrobial agents and oxygenating agents and their pairing. The significant properties are set forth in the tables below:

TABLE 1

| | USE CONCENTRATION (%) | | |
|---|---|---|---|
| | COMMERCIAL OR STANDARD | RANGE | PREFERRED RANGE |
| ANTIMICROBIAL AGENT | | | |
| Cetylpyridinium chloride | 0.05 | 0.01–0.5 | 0.02–0.10 |
| Polyvinylpyrrolidone-iodine complex (10% $I_2$) as % $I_2$: | 0.5–10.0 | 0.5–20.0 | 1.2–12.0 |
| | 0.05–1.0 | 0.05–2.0 | 0.12–1.2 |
| Biopal iodophor (as % $I_2$) | 2.0 | 0.25–10.0 | 0.60–5.0 |
| OXYGENATING AGENT | | | |
| Carbamide Peroxide | 4.15 | 1.5–30.0 | 3–12 |
| Hydrogen Peroxide | 1.5 | 0.5–10.0 | 1–4 |

TABLE 2 pH OF ANTIMICROBIAL AND OXIDIZING AGENTS, SINGLY AND IN COMBINATION

| | | | | pH in combination with: | |
|---|---|---|---|---|---|
| Agent | diluent* | MBC (conc. %) | pH alone | $H_2O_2$ | Carbamide peroxide |
| Biopal iodophor | w | 2.0 | 7.1 | 3.5 | 5.5 |
| Cetylpyri- | w | 20.0 | 3.9 | 3.0 | 4.8 |

TABLE 2-continued pH OF ANTIMICROBIAL AND OXIDIZING AGENTS, SINGLY AND IN COMBINATION

| Agent | diluent* | MBC (conc. %) | pH alone | pH in combination with: $H_2O_2$ | Carbamide peroxide |
|---|---|---|---|---|---|
| dinium chloride |  |  |  |  |  |
| PVP—I | w | 1.0 | 5.1 | 5.3 | 5.8 |
| Carbamide peroxide | w | 50.0 | 5.4 | — | — |
| Hydrogen peroxide | w | 24.0 | 2.9 | — | — |

*w = distilled water

TABLE 3

MBC of Antimicrobial Agents and Oxidizing Agents against *Bacteroides gingivalis*, *Bacteroides intermedius* and *Actinomyces viscosus*

| Agents | Mode MBCs (% conc.)* B. gingivalis | B. intermedius | A. viscosus |
|---|---|---|---|
| Cetylpyridinium chloride | 1.0 | >20.0 | 1.0 |
| Biopal iodophor | 1.0 | 2.0 | 4.8 |
| PVP—I | 1.0 | 1.0 | 0.5 |
| $H_2O_2$ | 17.5 | 24.0 | 30.0 |
| Carbamide peroxide | 30.0 | 50.0 | >12.0 |

*mode MBC based on minimum of 4 replicates

Table 1 indicates use concentrations of the antimicrobial and of oxygenating agent components which can comprise pairs for various lavage mixtures.
Table 2 indicates the pH of the agents singly and in combination.
Table 3 sets forth the MBC's of the antimicrobial agents and the oxidizing agents against the specified microorganisms.

TABLE 4a

Fractional Bactericidal Concentration (FBC) Index of Antimicrobials in Combination with $H_2O_2$ against *B. gingivalis*

| Agent | Concn. of individual agent at MBC of combination:* Antimicrobial | $H_2O_2$ | FBC index | Effect |
|---|---|---|---|---|
| Cetylpyridinium chloride** | 0.5 | 4.4 | 0.5–1.0 | greater than additive |

TABLE 4a-continued

Fractional Bactericidal Concentration (FBC) Index of Antimicrobials in Combination with $H_2O_2$ against *B. gingivalis*

| Agent | Concn. of individual agent at MBC of combination:* Antimicrobial | $H_2O_2$ | FBC index | Effect |
|---|---|---|---|---|
| Biopal iodophor | 0.25 | 4.4 | 0.5 | greater than additive |

*MBC of combination based on minimum of 4 replicates
**zones difficult to interpret due to membrane discoloration by agent

TABLE 4b

Fractional Bactericidal Concentration (FBC) Index of Antimicrobials in Combination with Urea peroxide against *B. gingivalis*

| Agent | Concn. of individual agent at MBC of combination:* Antimicrobial | Carbamide Peroxide | FBC index | Effect |
|---|---|---|---|---|
| Cetylpyridinium chloride** | 1.0 | 15.0 | 1.0 | additive |
| Biopal iodophor | 0.25* | 7.5 | 0.5 | greater than additive |
| PVP—I | 0.25 | 7.5 | 0.5 | greater than additive |

MBC of combination based on minimum of 4 replicates
*zones difficult to interpret due to membrane discoloration by agent

TABLE 5a

Fractional Bactericidal Concentration (FBC) Index of Antimicrobials in Combination with $H_2O_2$ against *Bacteroides intermedius*

| Agent | Concn. of individual agent at MBC of combination:* Antimicrobial | $H_2O_2$ | FBC index | Effect |
|---|---|---|---|---|
| Cetylpyridinium | >10.0 | >12.0 | nd | nd |
| Biopal iodophor | 0.5 | 6.0 | 0.5 | greater than additive |

ªMBC's of combination based on minimum of 4 replicates
**zones difficult to interpret due to membrane discoloration
nd = not determined

TABLE 5b

Fractional Bactericidal Concentration (FBC) Index of Antimicrobials in Combination with Urea Peroxide against *Bacteriodes intermedius*

| Agent | Concn. of individual agent at MBC of combination:* Antimicrobial | Carbamide Peroxide | FBC index | Effect |
|---|---|---|---|---|
| Cetylpyridinium chloride** | >10.0 | >25.0 | nd | additive |
| Biopal iodophor | 0.5 | 12.50* | 0.5 | greater than additive |
| PVP—I | 0.12 | 12.50* | 0.5 | greater than additive |

*MBC's of combination based on minimum of 4 replicates
**zones difficult to interpret due to membrane discoloration by agent
nd = not determined In practice, the oral lavages of this invention function to improve antisepsis of the teeth and gums. This action ensures that more effective protection is maintained in the interim between normal periodic visits for professional dental care. In many cases, as a result of such everyday self-care by the individual himself, the professional care required during such visits is minimized.

In carrying out this invention, the above described ingredients for preparing the oral lavages in the above described proportions are provided or prepared in separate packages or composite containers, each package containing one of the described ingredients in the measured amounts desired and each composite container having the components therein separated by a frangible section which when ruptured allows formation of the admixture of components or, alternatively, both components can be premixed with an added stabilizer to avoid premature interaction. Prior to use, each of the packages is opened or connected, the contents are admixed in a single vessel and appropriately applied to the teeth and gums by rinsing or irrigation. In the present state of the packaging technology, it is possible to package each liquid ingredient in the desired amount in a single segmented container or package having a common frangible or rupturable barrier or partition. Each of the separate compartments may be manually broken, and the contents admixed within or outside of the package and supplied to the teeth and gums as an oral lavage. When use is desired, the barrier or partition may be readily broken or perforated and both ingredients admixed within the container and subsequently applied to the mouth as an oral lavage. When the container or package has a pre-mixed stabilized composition therein, the composition is expelled or discharged into a receptacle and is then ready for use. The discharge may be carried out by a known aerosol dispenser.

The oral lavages of this invention when prepared and used as described, provide an unexpectedly improved cleansing effect upon the gums and surfaces of teeth, thereby altering the spectrum of aerobic and anaerobic microorganisms on such surfaces.

Some people, more than others, have a greater propensity for bacterial-caused diseases of the mouth, teeth and periodontium. The use of the oral lavages herein described is particularly advantageous for these people. The protection achieved by periodic visits for ordinary professional care by these people is substantially enhanced in the interim periods by frequent use of the oral lavage of this invention.

In some cases, the necessity for the application of restoratory and reconstructive procedures is substantially reduced with regular application of the oral lavage of this invention. Evidence of other oral diseases is also substantially decreased due to the interfunctional activity of each of the components of the oral lavage of this invention.

What is claimed is:

1. A non-toxic, cosmetically acceptable lavage for the treatment of periodontal disease comprising an antimicrobial agent selected from PVP-I, (nonyl-phenoxypoly (ethyleneoxy) ethanol iodine complex) per MPEP 608.01(V) "Trademarks and names" or cetylpryridinium chloride effective against the microorganisms normally present in the oral cavity admixed with a source of nascent or active oxygen comprising $H_2O_2$, carbamide peroxide, benzoyl peroxide or sodium peroxycarbonate, the antimicrobial agent and the oxygen source being in predetermined relative amounts and proportions and maintained out of contact with one another until they are to be combined to form the oral lavage or pre-mixed as a stabilized combination, the antimicrobial agent and the oxygen source interacting when the lavage is ready to be used such that the oxygen source leases oxygen to enhance the antimicrobial activity of the antimicrobial agent.

2. An oral lavage according to claim 1 wherein the antimicrobial agent is PVP-I.

3. An oral lavage according to claim 1 wherein the antimicrobial agent is (nonyl-phenoxypoly (ethyleneoxy) ethanol iodine complex) per MPEP 608.01(V) "Trademarks and names".

4. An oral lavage according to claim 1 wherein the antimicrobial agent and the oxygen source are in the proportional ratio of 1:1 (v/v).

5. An oral lavage according to claim 1 wherein the source of nascent or active oxygen is $H_2O_2$, carbamide peroxide, benzoyl peroxide or sodium peroxycarbonate.

6. An oral lavage according to claim 1 wherein the oxygen source is $H_2O_2$.

7. An oral lavage according to claim 1 wherein the antimicrobial agent is povidone iodine and the oxygen source is carbamide peroxide.

8. A method of preparing an oral lavage of claim 1 which comprises dissolving a predetermined amount of the antimicrobial agent in water and combining it with a solution of the oxygen source in water, the solutions prior to admixture thereof being packaged in physically separated form from one another or pre-mixed as a stabilized combination until ready for use and application to the teeth and periodontium.

9. A method of preparing an oral lavage of claim 1, wherein the antimicrobial agent is an iodine complex or quaternary ammonium compound and the oxygen source is hydrogen peroxide or carbamide peroxide.

10. A method of preparing an oral lavage of claim 1, wherein the antimicrobial agent is (nonyl-phenoxypoly (ethyleneoxy ethanol rupine complex) per MPES 608.01(V) "Trademarks and names" and the oxygen source is hydrogen peroxide.

11. A method of preparing an oral lavage of claim 1, wherein the antimicrobial agent is cetylpyridinium chloride and the oxygen source is carbamide peroxide.

12. A method of preparing a packaged oral lavage of claim 1 which comprises producing a pre-mixed stabilized combination of a solution of a predetermined amount of a water-soluble antimicrobial agent comprising PVP-I or (nonyl-phenoxypoly (ethyleneoxy) ethanol iodine complex) per MPEP 608.01(V) "Trademarks and names" or cetylpyridinium chloride and a solution of a source of nascent or active oxygen and packaging the pre-mixed combined solutions under conditions preventing premature contact, interaction or decomposition of the combined packaged solutions.

13. A method of controlling *Actinomyces viscosus, Bacteroides intermedius, Bacteroides gingivalis, Fusobacterium nucleatum* or *Actinomyces viscosus* implicated as microorganisms in diseases of the periodontium which comprises applying by rinsing or irrigating an oral lavage in accordance with claim 2 produced by dissolving a predetermined amount of the antimicrobial agent in water and combining it with a solution of the oxygen source in water, the solutions prior to admixture thereof being packaged in physically separated form from one another or pre-mixed as a stabilized combination until ready for use and application to the teeth and periodontium for a period of time ranging from about 10–40 seconds for each rinsing application and about 2–5 minutes for each irrigation and in an amount sufficient to thoroughly wet the tissues of the gum, thereby destroying or inactivating the microorganisms and reducing or retarding plaque and cavity formation on the teeth.

14. The method of claim 13 wherein the oral lavage is applied to the periodontium and teeth by a rinsing action for one or more periods daily of about 30 seconds followed by expectoration.

15. The method of claim 13 wherein the oral lavage is applied to the gums and teeth by irrigation for about 2–5 minutes.

16. Antimicrobial means for controlling diseases of the teeth and periodontium which comprises an aqueous solution of an admixture of predetermined proportions of an antimicrobial agent selected from PVP-I and Biopal (nonyl-phenoxypoly (ethyleneoxy) ethanol iodine complex) per MPEP 608.01(V) "Trademarks and names" and a source of nascent or active oxygen capable of releasing oxygen to enhance the antimicrobial action of the iodine derived from the antimicrobial agent, each of which is maintained out of contact with the other prior to their admixture and which upon admixture form a highly active aqueous antimicrobial solution characterized by cidal action against a wide spectrum of microorganisms implicated in periodontal diseases.

17. A non-toxic cosmetically acceptable antimicrobial lavage of enhanced activity for controlling diseases of the teeth and periodontium comprising as its effective components an aqueous solution containing the $+N_4$ ion of a quaternary ammonium compound or iodine derivable from an iodophor of claim 1 and a peroxide, the lavage being packaged with the components in separate compartments adapted to be combined to form the lavage upon opening or breaking of the package and emptying the contents of the compartments into a receptacle.

18. A non-toxic cosmetically acceptable antimicrobial lavage of enhanced activity for controlling diseases of the teeth and periodontium comprising as its effective components an aqueous solution containing the $+N_4$ ion of a quaternary ammonium compound or iodine derivable from an iodophor of claim 1 and a peroxide, the lavage being packaged as a stabilized combination in a single compartment package which is openable to empty the contents into a receptacle.

* * * * *